US006530765B1

United States Patent
Zdrahala et al.

(10) Patent No.: US 6,530,765 B1
(45) Date of Patent: *Mar. 11, 2003

(54) APPARATUS FOR MANUFACTURING EXPANDED POLYTETRAFLUOROETHYLENE PRODUCTS

(75) Inventors: Richard J. Zdrahala, Montville, NJ (US); Nick Popadiuk, Hillsborough, NJ (US); David J. Lentz, Randolph, NJ (US); Edward J. Dormier, Rockaway, NJ (US)

(73) Assignee: Meadox Medicals, Inc., Oakland, NJ (US)

( * ) Notice: Subject to any disclaimer, the term of this patent is extended or adjusted under 35 U.S.C. 154(b) by 157 days.

This patent is subject to a terminal disclaimer.

(21) Appl. No.: 09/595,548

(22) Filed: Jun. 16, 2000

Related U.S. Application Data

(63) Continuation of application No. 09/245,210, filed on Feb. 5, 1999, now abandoned, which is a continuation of application No. 08/545,799, filed as application No. PCT/US95/03018 on Mar. 9, 1995, now Pat. No. 5,874,032, said application No. 09/245,210, is a continuation-in-part of application No. 08/209,543, filed on Mar. 10, 1994, now Pat. No. 5,505,887.

(51) Int. Cl.[7] ............................................. B29C 47/24
(52) U.S. Cl. ................... 425/144; 425/381; 425/378.1; 425/467
(58) Field of Search ............................ 425/378.1, 381, 425/144, 467

(56) References Cited

U.S. PATENT DOCUMENTS

| | | | |
|---|---|---|---|
| 2,736,064 A | 2/1956 | Rubin | 264/210.2 |
| 2,945,265 A | 7/1960 | Sell et al. | 264/127 |
| 3,008,187 A | 11/1961 | Slade | 264/119 |
| 3,085,290 A | 4/1963 | Chu | 264/127 |
| 3,260,774 A | 7/1966 | Harlow | 264/28 |
| 3,382,220 A | 5/1968 | Bowman, Jr. | 428/36.9 |
| 3,404,203 A | 10/1968 | Donald | 264/108 |
| 3,508,554 A | 4/1970 | Sheridan | 604/523 |
| 3,651,187 A | 3/1972 | Cessna, Jr. | 264/108 |
| 3,907,955 A | 9/1975 | Viennot | 264/105 |
| 3,950,118 A | 4/1976 | Adair | 425/144 |
| 4,104,394 A | 8/1978 | Okita | 264/568 |
| 4,151,242 A | 4/1979 | Sansone | 264/68 |
| 4,225,547 A | 9/1980 | Okita | 264/127 |
| 4,250,138 A | 2/1981 | Okita | 264/568 |
| 4,482,516 A | 11/1984 | Bowman et al. | 264/127 |
| 4,647,416 A | 3/1987 | Seiler, Jr. et al. | 264/118 |
| 4,743,480 A | 5/1988 | Campbell et al. | 428/36.5 |
| 4,876,051 A | 10/1989 | Campbell et al. | 264/127 |
| 5,059,375 A | 10/1991 | Lindsay | 264/167 |
| 5,098,625 A | 3/1992 | Huang et al. | 264/127 |
| 5,156,785 A | 10/1992 | Zdrahala | 264/108 |
| 5,169,587 A | 12/1992 | Courval | 264/323 |
| 5,505,887 A | 4/1996 | Zdrahala et al. | 264/127 |
| 5,874,032 A | 2/1999 | Zdrahala et al. | 264/127 |

FOREIGN PATENT DOCUMENTS

| | | | | |
|---|---|---|---|---|
| GB | 1170564 | 11/1969 | | 105/14 |
| JP | A52-72765 | 6/1977 | | B29F/3/014 |
| JP | A61-143112 | 6/1986 | | |
| WO | WO 94/15781 | 7/1994 | | B32B/3/26 |

Primary Examiner—Jan H. Silbaugh
Assistant Examiner—Joseph S Del Sole
(74) Attorney, Agent, or Firm—Hoffmann & Baron, LLP

(57) ABSTRACT

An improved method and apparatus is provided for extruding ePTFE tube for use in medical applications. A tube of PTFE is extruded, preferably in an extrusion process, using counter-rotated die components. The die component is maintained at a constant temperature during processing. The resulting green tube has enhanced fibrous state formation in a direction perpendicular to the direction of extrusion. The PTFE green tube is then subjected to secondary operations such as stretching and expansion to yield medical product. The ePTFE tube structure is defined by nodes interconnected by elongate fibrils. Both the nodes and fibrils are substantially randomly tilted with respect to the longitudinal axis of the tube. This particular structure yields a tube which exhibits a high degree of radial tear strength useful in medical applications.

8 Claims, 3 Drawing Sheets

← Expansion Direction →

← Expansion Direction →

APPARATUS FOR MANUFACTURING EXPANDED POLYTETRAFLUOROETHYLENE PRODUCTS

This application is a continuation of copending application Ser. No. 09/245,210, filed on Feb. 5, 1999 now abandoned; which is a continuation of Ser. No. 08/545,799, filed on Apr. 15, 1996, now U.S. Pat. No. 5,874,032; which is a § 371 of PCT/US95/03018, filed Mar. 9, 1995; and said Ser. No. 09/245,210 filed Feb. 5, 1999, abandoned is a continuation-in-part of Ser. No. 08/209,543, filed Mar. 10, 1994, now U.S. Pat. No. 5,505,887.

FIELD OF THE INVENTION

The present invention relates generally to extruded PTFE products. More particularly the present invention relates to expanded PTFE products formed from an extrusion process, such products being useful in grafts, patches, tubing and the like specifically in medical applications.

BACKGROUND OF THE INVENTION

The use of products formed of polytetrafluoroethylene (PTFE) in medical applications is well known. Products such as implantable grafts, implantable patches, catheter tubing and the like may be derived from extruded tubing of PTFE.

PTFE tubing is normally manufactured by a paste extrusion process. Screw injection extrusion which is typical of most thermoplastics may not be effectively used with PTFE because PTFE resin does not exhibit sufficient fluidity even when heated. In the paste extrusion process a "green tube" is formed. A green tube is a tube of PTFE that must be subjected to secondary operations before it yields a usable medical product. Such secondary operations may include stretching and expanding the tube under various conditions of time, pressure and temperature. The paste extrusion process tends to produce a tube which has a fibrous state where its fibrils are generally longitudinally aligned in the direction of extrusion. This fibrous state formation is particularly evident where the PTFE paste includes a lubricant to assist in extrusion. Extruded tubes having fibrils longitudinally aligned in this fashion exhibit low radial or hoop strength. Such a tube is highly susceptible to tearing or rupturing.

Attempts have been made to modify the structure of extruded PTFE tubing. Such attempts seek to manufacture extruded PTFE tubing having non-longitudinally aligned fibrils where the fibrous state formation includes fibrils aligned transversely to the extrusion direction. One attempt in the vascular graft art is shown in U.S. Pat. No. 4,743,480. This technique employs a screw tip on the extrusion mold to reorient the fibrils during the paste extrusion process. The pitch of the screw tip tends to twist the fibrils during extrusion.

In the mechanical art area, U.S. Pat. No. 4,225,547 employs counter-rotation to manufacture pipes and wire jackets. In this example, the mandrel and the outer portion of the extrusion die are counter-rotated with respect to one another. While this tends to orient the fibrils in both the longitudinal and transverse direction, as set forth in the '547 patent a suitable product is only obtained by establishing during extrusion a temperature gradient where the die temperature is substantially higher than the initial temperature of the paste preform entering the die apparatus.

In this process, the die is therefor heated to a temperature significantly above the initial paste temperature. As is set forth in the '547 patent, elevating the temperature of the die over that of the incoming paste while counter rotating the die components, subjects the product to thermal expansion and enhances the fibrous-state formation in the direction perpendicular to the direction of extrusion.

However, the process described in the '547 patent has several disadvantages. First, it is difficult to maintain predictable processing parameters where a temperature gradient is relied upon. Further, it is difficult to maintain an environment where a temperature gradient must be established and maintained. In addition frictional heating of the paste due to contact with rotational members precludes establishment of a reproducible steady state extrusion condition where a fixed temperature gradient must be maintained. Finally, the compressible nature of PTFE pastes, coupled with their high coefficient of expansion make operation under a fixed temperature gradient highly undesirable.

It is therefore desirable to provide a process for producing a PTFE tube where fibrous-state formation is enhanced thereby resulting in a tube having higher radial is strength, without the need to maintain a precise temperature gradient during processing.

SUMMARY OF THE INVENTION

It is an object of the present invention to provide an improved method and apparatus for forming a PTFE tubular product in a paste extrusion process.

It is a further object of the present invention to provide an expanded PTFE product (ePTFE) formed by an improved process which exhibits high radial tear strength.

It is a still further object of the present invention to provide an ePTFE product having a microporous structure with substantially randomly tilted fibril and node structure.

In the efficient attainment of these and other objects the present invention provides an improved method and apparatus for forming a PTFE tubular product. The present invention provides for the extrusion of a PTFE green tube between at least one rotating die of an extrusion apparatus. The extrusion apparatus is maintained at a constant temperature to avoid a temperature gradient during extrusion. The die components may be rotated during extrusion to enhance fibrous state formation of the tube in a direction generally perpendicular to the extrusion direction. The green tube so formed may be then subjected to secondary operations such as stretching and expanding to form an ePTFE tube suitable for medical use. The ePTFE tube exhibits a microporous structure defined by nodes interconnected by elongate fibrils. The nodes in such a microporous structure are oriented such that their primary axes are not generally perpendicular to the longitudinal axis of the tubular body.

DETAILED DESCRIPTION OF THE PREFERRED EMBODIMENT

The present invention contemplates providing a "green tube" having desirous fibrous state formation i.e. fibrous state formation which is generally more perpendicular to the direction of extrusion than is traditionally achieved, without the need to establish and maintain a temperature differential between the incoming preform paste and the extrusion die as is required in prior art practices. The present invention provides for the manufacture of PTFE green tube in an environment where the die apparatus is maintained at substantially a uniform, constant temperature. It is within the contemplation of the present invention to provide such uniform temperature either at ambient temperature or above or below ambient temperature as will be evidenced from the following description.

Figure 1:
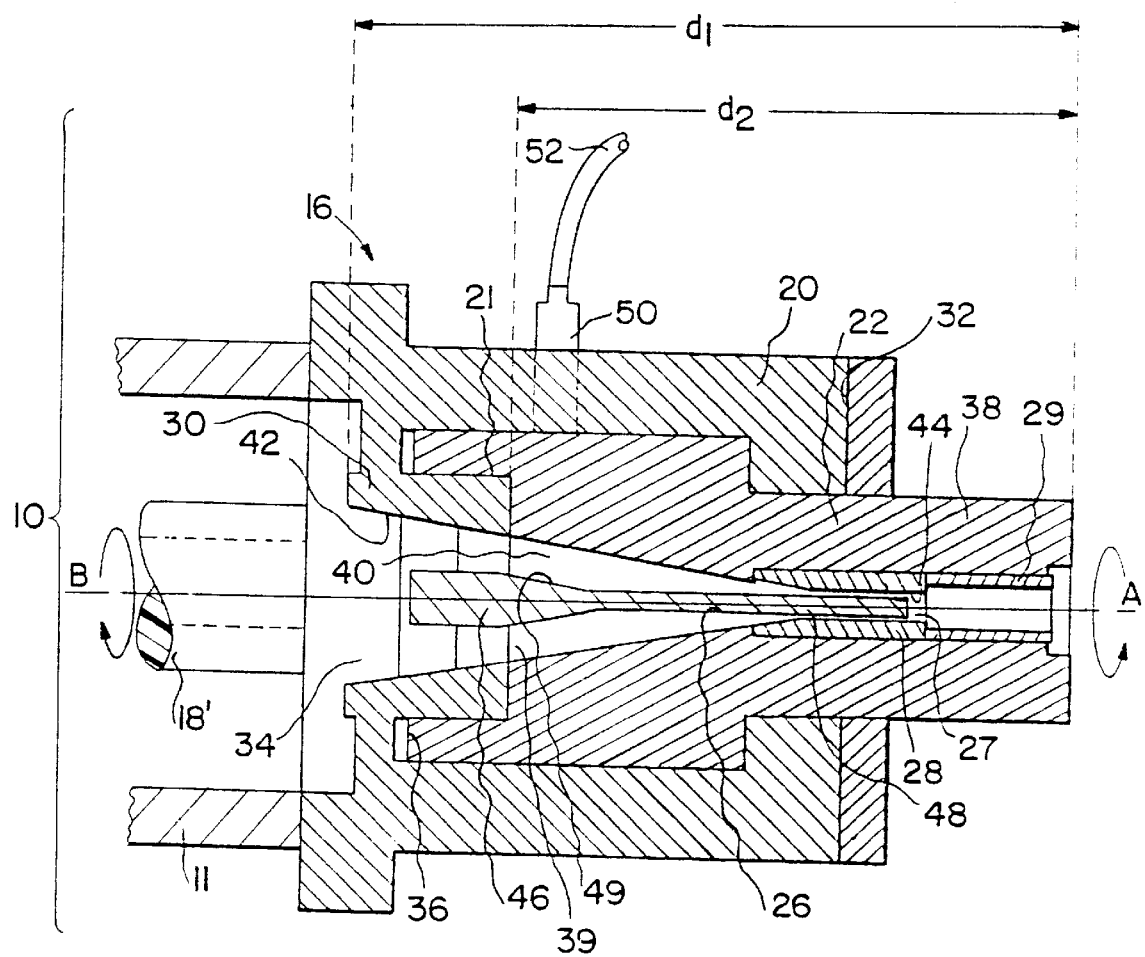
FIG. 1 shows in schematic section, the die apparatus used to extrude a PTFE tube.

An extrusion apparatus 10 used to form an extruded PTFE tube 12 (FIG. 3) is shown with reference to FIG. 1. The extrusion apparatus 10 includes a conventional extruder 11 which accepts PTFE paste. As stated above, the process of the present invention employs a paste extrusion process where PTFE resin is mixed with liquid lubricant. As is well known in the PTFE extrusion art, a lubricant is used to render the PTFE paste more fluid and easier to extrude and handle after it is formed into a tube. A PTFE paste of resin and lubricant is formed in a preform press (not shown) into a preform product referred to as a tubular billet 18. Tubular billet 18 is loaded into the extruder 11 in a position where it may be fed into a die apparatus 16 in a manner which is also well known in the extrusion art.

In the present invention, die apparatus 16 is a multi-component device including a stationary die body 20, a rotating die element 22, a supporting plate 24 which supports die element 22 to die body 20, a mandrel 26, a die insert 28 and an insert spacer 29. Each of the die apparatus components are typically formed of metal, preferably stainless steel.

Die body 20 is generally an elongate hollow cylindrical member having a first end 30 for receiving billet 18, a second end 32 for rotationally supporting die element 22 and a central bore 34 therethrough. Die body 20 is supported by the extruder 11 in a fixed non-movable position with respect thereto.

Die element 22 is generally an elongate hollow cylindrical member having a first end 36 which is supported adjacent first end 30 of die body 20. Die element 22 also includes an opposed second end 38 which extends outwardly beyond second end 32 of die body 20. A central bore 39 is defined between the first end 36 and the second end 38 of die element 22. Bore 39 of die element 22 is in communication with bore 34 of die body 20 and together with mandrel 26 define a generally narrowing annular extrusion bore 40 for passage of tubular billet 18 in a manner which will be described in further detail hereinbelow.

Supporting plate 24 secures die element 22 to die body 20. Various fastening techniques may be used to support supporting plate 24 to die body 20 to secure die element 22 thereto.

Die apparatus 16 further includes an elongate hollow generally cylindrical die insert 28 positioned within bore 39 of die element 22 adjacent second end 38 thereof. Die insert 28 has a central bore 27 therethrough. As will be described in further detail hereinbelow, die insert 28 is used to form and regulate the outside dimension (O.D.) of tube 12 which is extruded through die apparatus 16. Die insert 28 may be interchanged with differently sized die inserts to vary the O.D. of tube 12 formed thereby.

A die spacer 29 is used to support and position die insert 28 within bore 39 of die element 22.

Bore 34 of die body 20, bore 39 of die element 22 as well as bore 27 of die insert 28 are each longitudinally aligned in successive communicative position, and together with mandrel 26 form a die cavity coextensive with elongate extrusion bore 40 for the passage of tubular billet 18. Extrusion bore 40 is generally conical in shape having a wider end 42 for receiving billet 18 and a narrow cylindrical end 44 for the formation of tube 12.

Mandrel 26 of die apparatus 16 is an elongate generally cylindrical member centrally positioned within bore 40. A cylindrical end 46 of mandrel 26, adjacent first end 30 of die body 20, is wider than the opposite cylindrical end 48 adjacent die insert 28. A central conically tapered section 49 of mandrel 26 provides a transition between wider end 46 and narrower opposite end 48. Cylindrical end 48 of mandrel 26 is positioned centrally within bore 27 of die insert 28 and forms the inner diameter (I.D.) of tube 12.

As described above, die element 22 is supported within die body 20 for relative rotational movement with respect thereto. As die element 22 is constructed to rotate with respect to die body 20, a resilient sealing member (not shown) may be interposed between the interface 21 of the two components to form a seal thereat.

A conventional mechanism (not shown) may be secured to die element 22 to permit the rotational movement thereof. Further, a similar conventional mechanism (also not shown) may be secured to mandrel 26 to permit its rotational movement. Die element 22 and mandrel 26 are designed to be rotated in either the same rotational direction (co-rotation) or opposite relative rotational directions (counter-rotation). It is also contemplated that only one of die element 22 or mandrel 26 may be rotated.

As shown in FIG. 1 in a preferred embodiment, die element 22 may be rotated in the rotational direction of arrow A, while mandrel 26 may be rotated in the rotational direction of arrow B, which is opposite of arrow A. As will be described in further detail hereinbelow, the conventional mechanisms used to rotate die element 22 and mandrel 26 may also vary the rotational speeds of each of die element 22 and mandrel 26.

The present invention further contemplates varying the length of the rotating outer portion of die apparatus 16, by varying the length of rotating die element 22. As shown in FIG. 1, bore 40 defined between first end 30 of die body 20 and the second end 38 of die element 22 along center line l, has an overall length of $d_1$. A portion $d_2$ of this length, defined solely by rotating die element 22, is rotatable. In the present illustrative example $d_2$ may be between about 10% and 100% of $d_1$. It has been found that results such as those described hereinbelow may be varied by varying the length of the rotating portion of die apparatus 16.

As mentioned above, the present invention provides for the ability to maintain the extrusion apparatus 10 at a uniform constant temperature so that there is no temperature variation in the PTFE paste between the tubular billet stage and the final green tube stage. While such controlled temperature may be at ambient temperature or an elevated or cooled temperature, it does not substantially vary throughout the extrusion process. In that regard, die body further includes temperature control connection ports 50 thereon. Connection ports 50 connect fluid tubes 52 to die body 20. This permits a temperature controlled liquid to be circulated around die body 20 so as to control the temperature of the die apparatus 16 during the extrusion process. The rotative movement of mandrel 26 and die element 22 generates frictional heat which would be imparted to the tube 12 extruded therebetween. By circulating a temperature controlled medium throughout die apparatus 16, maintenance of temperature is achieved.

Where a controlled temperature at or below ambient is desired, typically a coolant is circulated through ports 50. This coolant is sufficient to maintain the die components at a temperature which would be lower than that normally achieved by the operation of the components. Where the desired controlled temperature is above ambient, the elevated temperature may be achieved by passing a warm solution through ports 50 or may be achieved by allowing the temperature of die components to rise (due to friction of the moving parts), in a controlled manner during use. In either case, the temperature of extruder 11 may also be elevated by any conventional heating source so as to maintain a constant temperature throughout processing.

Having described the structure of die apparatus 16, its operation may now be described.

Preformed tubular billet 18 is loaded into the extruder 11. Mandrel 26 is caused to rotate in the direction of arrow B and die element 22 is caused to rotate in the direction of arrow A. While providing such simultaneous counter-rotation of mandrel 26 and die element 22, tubular billet 18 is extruded through the bore 40. The extruded PTFE paste passes through die insert 28 to take the tubular shape shown in FIG. 3. The exiting tubular extrusion may be cut to any desired length.

As described above, conventional extrusion processes have a tendency to align the fibrils of extruded product along the direction of extrusion. Fibrils aligned in this manner result in a tube having low radial strength. By rotating the mandrel and the die, (particularly by counter-rotation) a structure of tube 12 is formed having generally non-aligned fibrils (FIG. 3) which increase the radial tear strength of the tube. The rotation of die element 22 imparts a helical fibril pattern to the outside of tube 12. Similarly rotation of mandrel 26 imparts a helical fibril pattern to the inside of tube 12. Where such rotation is counter-rotation, the helical pattern on the inside of tube 12 is opposite the helical pattern of the outside of the tube.

However, in the prior art practices of rotating die components, the desired non-aligned fibril structure is formed in an environment where an elevated temperature gradient is maintained. Such elevated temperature gradient could be externally induced or could be caused by the normal friction between the rotating parts. The present invention provides an extruded tube 12 having a desired non-aligned fibril structure without subjecting the die components to a temperature gradient. While the PTFE paste is being extruded through the die apparatus 16, it is maintained at a uniform temperature. By passing a temperature controlled fluid through tube 52 and ports 50 during extrusion as above described, the die apparatus 16 may be controlled and maintained at a substantially uniform temperature.

Figure 3:
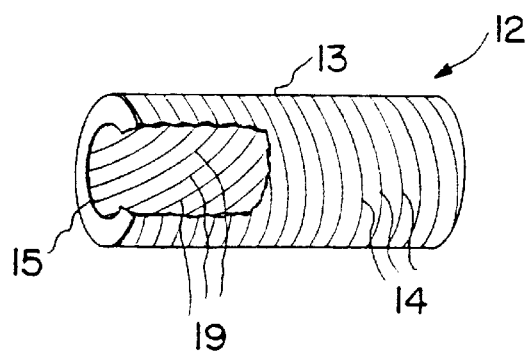
FIG. 3 is a perspective view partially broken away, of a PTFE tube formed in accordance with the present invention, showing schematically the fibrous state formation of the extruded tube.

Referring to FIG. 3, the fibrous structure of the tube 12 of the present invention is schematically represented. Tube 12 formed in accordance with the present invention shows the results of the preferred counter rotating of die element 22 with respect to mandrel 26 during extrusion. The outer surface 13 of tube 12 has fibril orientation 14 generally in a helical pattern. The direction of the helical fibril orientation 14 corresponds to the rotation direction A of die element 22 resulting from the outer surface 13 of tube 12 being in contact with rotating second die element 22 during extrusion. Similarly, the inner surface 15 of tube 12 has a fibril orientation 19 in a helical pattern which is opposite that of fibril orientation 14 on the outer surface 13 of tube 12. The helical pattern on inner surface 15 corresponds to rotation direction B of mandrel 26 resulting from the inner surface 15 of tube 12 being in contact with rotating mandrel 26 during extrusion. As rotation direction A is opposite that of rotation direction B, the helical fibril orientation 14 and 19 are also opposite one another. With respect to both outer surface 13 as well as inner surface 15 of tube 12, the effect of counter-rotation on the fibril orientation can be seen. Significant fibril orientation in a non-longitudinally aligned position is achieved.

It is further contemplated that different degrees of helical fibrous structure may be achieved by varying the relative rotational rates of mandrel 26 and die element 22 (FIG. 1). Also, as above mentioned, the helical fibrous structure may also be changed by varying the length of the rotating die element 22 with respect to stationary die body 20. Additionally, the temperature of operation may also effect fibrous state formation. Generally, as the length of the rotating component is increased or as the relative rotation rates of the counter rotating parts is increased, an increase in the fibrous formation in a non-longitudinally aligned position may be observed with an associated increase in radial tear strength.

Table I summarizes the resulting radial tensile strengths imparted to a tube formed in accordance with the FIG. 1 embodiment of the present invention.

TABLE I

|  | Die (RPM) | Mandrel (RPM) | Radial Tensile (kg/mm$^2$) |
| --- | --- | --- | --- |
| Control | 0 | 0 | 0.014 |
| Sample 1 | 0 | 30 | 0.017 |
| Sample 2 | 104 | 125 | 0.031 |
| Sample 3 | 104 | 250 | 0.037 |
| Sample 4 | 153 | 260 | 0.049 |

Figure 2:
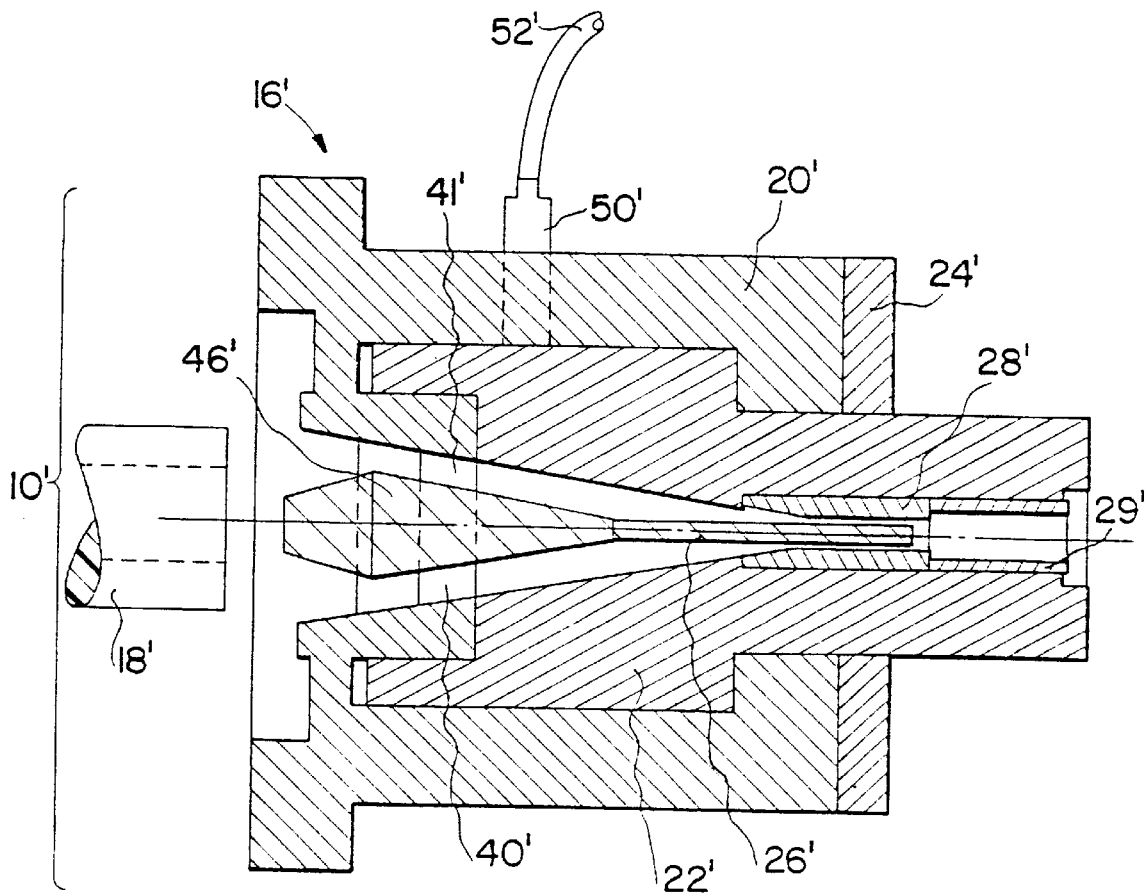
FIG. 2 shows in schematic section, a further embodiment of a die apparatus used to extrude a PTFE tube.

Referring now to FIG. 2, a further embodiment of the present invention is shown. Die apparatus 16' is substantially similar to die apparatus 16 shown in FIG. 1 (like reference numerals referring to like components). In the die apparatus 16' shown in FIG. 2, mandrel 26' is modified from that shown in FIG. 1. One end 46' of mandrel 26 is formed to have an overall conical configuration along a longitudinal extent 41'. End 46' is positioned such that extent 41' is aligned with a central portion of bore 40'. The conical configuration of extent 41' matches the conical configuration of bore 40' adjacent thereto. As wider end 46' now tapers to match the taper of bore 40' thereat, a generally uniformly tapering annual cavity extent is formed therebetween. This is in distinction to the embodiment shown in FIG. 1 where the wider end 46 of mandrel 26 is generally cylindrical while the bore 40 thereadjacent is tapered or conical.

In the embodiment shown in FIG. 2, it is contemplated that the extrusion of tubular billet 18' may be more easily facilitated through an annular bore which generally is of uniform bore width over a longitudinal extent. This reduces the tendency to force billet 18' into a chamber which abruptly narrows. The billet 18' is more easily passed through bore 40' with less resistance being encountered as the paste passes towards extrusion die 28'. This resulting ease of passage allows the mandrel 26' and die element 22' to be rotated at slower rates of rotation, i.e. slower RPM's, and still provide a suitable helical formation of the fibers during extrusion.

Table II summarizes the resulting radial tensile strength imparted to a tube formed in accordance with the FIG. 2 embodiment of the present invention.

TABLE II

| | Die (RPM) | Mandrel (RPM) | Radial Tensile (kg/mm$^2$) |
|---|---|---|---|
| Control | 0 | 0 | 0.014 |
| Sample 1 | 0 | 30 | 0.019 |
| Sample 2 | 10 | 20 | 0.020 |
| Sample 3 | 60 | 120 | 0.023 |
| Sample 4 | 125 | 250 | 0.026 |

In each of the embodiments described above, desirable fibrous state formation is achieved by preferably counter-rotating the die with respect to the mandrel. However as stated, it is contemplated that advantageous results may also be achieved by co-rotating the die with the mandrel. By extruding a PTFE tube through one or more rotating members, enhanced fibril formation in a direction generally perpendicular to the extrusion direction may be achieved even where the components are co-rotated.

Tube 12 shown in FIG. 3 and formed in accordance with either above-described embodiment of the present invention, is subjected to secondary operations in order to yield a usable medical product. It is well known to subject a tube of PTFE to secondary operations such as stretching and expansion in order to produce an expanded polytetrafluoroethylene tube (ePTFE). As is well known in medical applications, especially with respect to grafts, patches and other implantable devices, ePTFE products exhibit certain desirable characteristics such as increased strength especially in the direction of extrusion and better porosity.

In the present invention, the secondary operations such as stretching and expansion may take place a manner which is well known in the PTFE art.

Figure 4:
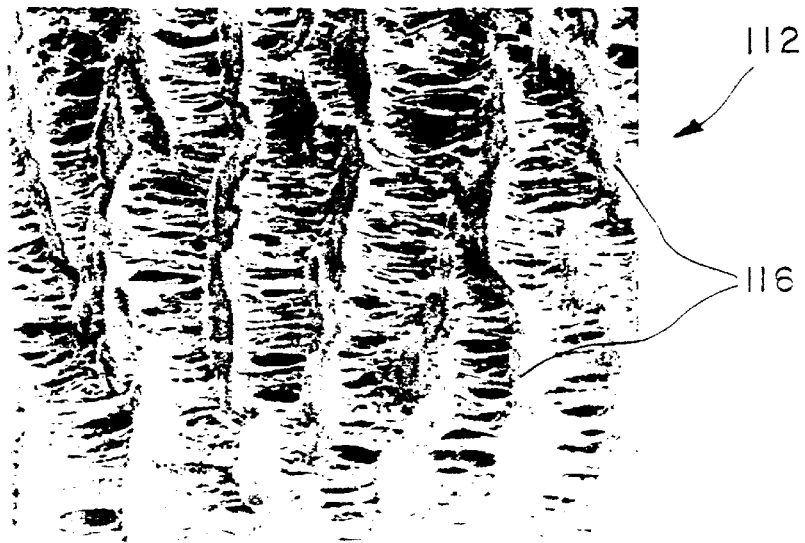
FIG. 4 is an electron micrograph of a portion of the outer surface of an expanded PTFE tube of the prior art.

FIG. 4 is an electron micrograph (900×) of the outer surface 112 of an expanded PTFE tube produced from a precursor green tube prepared using conventional PTFE extrusion technology. As is clear from this micrograph, all nodes 116 are oriented such that their primary axes are essentially perpendicular to the elongation direction. Such a high degree of structural anisotropy results in greater longitudinal strength as compared to radial strength.

Figure 5:
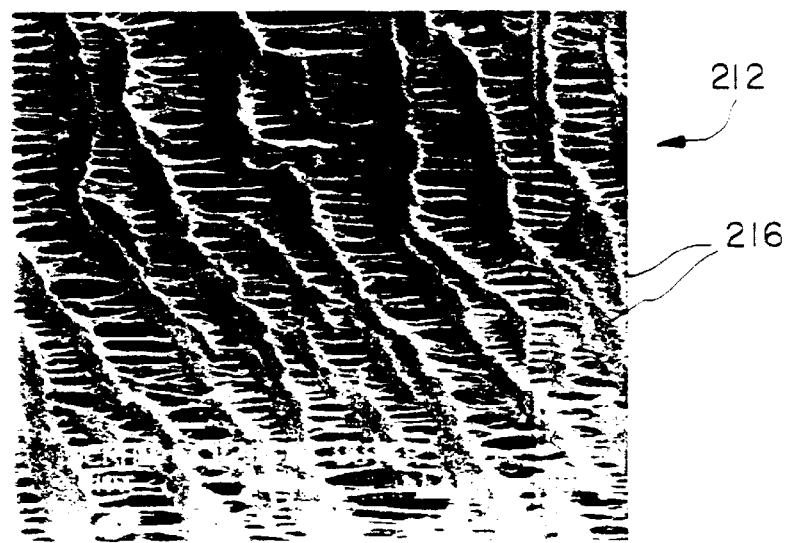
FIG. 5 is an electron micrograph of a portion of the outer surface of an expanded PTFE tube of the present invention.

In contrast, FIG. 5 is an electron micrograph (900×) of the outer surface 212 of an expanded PTFE tube produced from a precursor green tube prepared in accordance with the method described in the present invention. There is clearly a substantial tilting of the node structure 216 such that their primary axes are not exclusively perpendicular to the elongation direction. It is this increased randomness in the fibril/node structure, and specifically the non-perpendicular alignment of the nodes 216, which yields improved physical properties, especially regarding radial tensile strength of the ePTFE tube.

Table III summarizes the resultant strength of ePTFE tubes produced from an extruded tube prepared in accordance with the present invention.

TABLE III

| | Die (RPM) | Mandrel (RPM) | Radial Tensile (kg/mm$^2$) |
|---|---|---|---|
| Control | 0 | 0 | 0.55 |
| Sample 1 | 10 | 35 | 0.84 |
| Sample 2 | 20 | 85 | 1.00 |
| Sample 3 | 25 | 105 | 1.06 |
| Sample 4 | 40 | 200 | 1.14 |

Various changes to the foregoing described and shown structures would now be evident to those skilled in the art. Accordingly the particularly disclosed scope of the invention is set forth in the following claims.

What is claimed is:

1. A paste extrusion apparatus for forming a PTFE green tube from a tubular PTFE paste billet comprising:

an extrusion die defining a conical die cavity for accepting said PTFE paste billet at one end and for extruding said PTFE green tube from the other end;

an elongate mandrel concentrically located within said die cavity, said extrusion die and said mandrel defining an extrusion passageway therebetween;

rotating means for relatively rotating said die cavity with respect to said mandrel; and temperature control means for controlling the temperature at a substantially uniform constant temperature throughout said extrusion die so as to maintain said paste extruded therethrough at a uniform temperature.

2. An apparatus of claim 1 wherein said rotating means includes said mandrel being rotatable.

3. An apparatus of claim 2, wherein said rotating means includes said extrusion die being rotatable.

4. An apparatus of claim 1, wherein said rotating means includes said extrusion die and said mandrel being rotatable.

5. An apparatus of claim 4, wherein said extrusion die is counter rotatable with respect to said mandrel.

6. An apparatus of claim 4 wherein said extrusion die is co-rotatable with respect to said mandrel.

7. An apparatus of claim 1 wherein said temperature control means includes means for introducing fluid to said extrusion die.

8. An apparatus of claim 7 wherein said fluid introducing means includes a connection port providing fluid access to said extrusion die.

* * * * *

UNITED STATES PATENT AND TRADEMARK OFFICE
CERTIFICATE OF CORRECTION

PATENT NO. : 6,530,765 B1  Page 1 of 1
DATED : March 11, 2003
INVENTOR(S) : Zdrahala et al.

It is certified that error appears in the above-identified patent and that said Letters Patent is hereby corrected as shown below:

<u>Column 2,</u>
Line 19, delete "...radial is strength..." and insert -- radial strength --.

<u>Column 4,</u>
Line 57, delete "...die body further..." and insert -- die body 20 further --.

Signed and Sealed this

Twenty-first Day of October, 2003

JAMES E. ROGAN
*Director of the United States Patent and Trademark Office*